(12) United States Patent
Liao (10) Patent No.: US 7,978,191 B2
(45) Date of Patent: Jul. 12, 2011

(54) SYSTEM AND METHOD FOR LOCATING ANATOMIES OF INTEREST IN A 3D VOLUME

(75) Inventor: Swanwa Liao, Woodland Hills, CA (US)

(73) Assignee: Dolphin Imaging Systems, LLC, Chatsworth, CA (US)

(*) Notice: Subject to any disclaimer, the term of this patent is extended or adjusted under 35 U.S.C. 154(b) by 960 days.

(21) Appl. No.: 11/860,303

(22) Filed: Sep. 24, 2007

(65) Prior Publication Data

US 2009/0079738 A1   Mar. 26, 2009

(51) Int. Cl.
G06T 15/00 (2011.01)
G06T 17/00 (2006.01)
G06K 9/00 (2006.01)
A61B 6/00 (2006.01)
A61B 5/05 (2006.01)

(52) U.S. Cl. ............ 345/419; 345/420; 378/4; 382/128; 382/131; 600/425

(58) Field of Classification Search .................. 345/419, 345/420; 378/4; 382/128, 131; 600/425
See application file for complete search history.

(56) References Cited

U.S. PATENT DOCUMENTS

| | | | |
|---|---|---|---|
| 4,239,971 A | | 12/1980 | Cushman |
| 4,791,581 A | * | 12/1988 | Ohba .......................... 345/585 |
| 5,371,778 A | | 12/1994 | Yanof et al. |
| 5,462,068 A | | 10/1995 | Rijke et al. |
| 5,696,892 A | | 12/1997 | Redmann et al. |
| 5,722,408 A | | 3/1998 | Dehner et al. |
| 5,734,384 A | | 3/1998 | Yanof et al. |
| 5,745,197 A | * | 4/1998 | Leung et al. .................... 349/77 |
| 5,748,193 A | | 5/1998 | Higashi et al. |

(Continued)

FOREIGN PATENT DOCUMENTS

JP   08-212391   8/1996

(Continued)

OTHER PUBLICATIONS

International Search Report and Written Opinion dated Dec. 8, 2008 for PCT/US08/77570, 9 pgs.

Primary Examiner — Xiao M Wu
Assistant Examiner — David T Welch
(74) Attorney, Agent, or Firm — Christie, Parker & Hale, LLP (57) ABSTRACT

A system and method for modifying a curved cut plane of a 3D volume to locate objects or sections of interest within the 3D volume intersected by the cut plane. A cross-section of the 3D volume along an initially estimated curved cut plane is projected onto a flat viewing plane, and a panorama image of the cross-section is displayed to the user. If the initially estimated curved cut plane does not exactly intersect the object or section of interest, the user manipulates a user input device to modify the curve of the plane inward or outward in the 3D volume away from the projected plane. As the user manipulates the user input device, an affected portion of the curve is recalculated and a modified curved cut plane is reconstructed based on the recalculated curve for re-projecting a modified cross-section of the 3D volume in real time with the movement of the user input device. The user is therefore provided with instant visual feedback as the user moves the user input device to browse in and out within the 3D volume from the current projected plane.

21 Claims, 11 Drawing Sheets

U.S. PATENT DOCUMENTS

| | | | |
|---|---|---|---|
| 5,802,134 A | 9/1998 | Larson et al. | |
| 5,881,122 A | 3/1999 | Crawford et al. | |
| 6,002,738 A | 12/1999 | Cabral et al. | |
| 6,006,126 A * | 12/1999 | Cosman | 600/426 |
| 6,072,496 A | 6/2000 | Guenter et al. | |
| 6,081,739 A | 6/2000 | Lemchen | |
| 6,181,348 B1 | 1/2001 | Geiger | |
| 6,208,347 B1 | 3/2001 | Migdal et al. | |
| 6,212,420 B1 * | 4/2001 | Wang et al. | 600/407 |
| 6,421,413 B1 | 7/2002 | Knoplioch et al. | |
| 6,492,990 B1 | 12/2002 | Peleg et al. | |
| 6,493,415 B1 * | 12/2002 | Arai et al. | 378/4 |
| 6,545,678 B1 | 4/2003 | Ohazama | |
| 6,549,200 B1 | 4/2003 | Mortlock et al. | |
| 6,671,538 B1 | 12/2003 | Ehnholm et al. | |
| 6,690,371 B1 | 2/2004 | Okerlund et al. | |
| 6,879,323 B1 | 4/2005 | Takezawa et al. | |
| 6,879,712 B2 | 4/2005 | Tuncay et al. | |
| 7,016,461 B2 | 3/2006 | Rotondo et al. | |
| 7,031,505 B2 | 4/2006 | Accomazzi | |
| 7,155,042 B1 * | 12/2006 | Cowan et al. | 382/128 |
| 2001/0026637 A1 | 10/2001 | Lelong et al. | |
| 2002/0118869 A1 * | 8/2002 | Knoplioch et al. | 382/131 |
| 2003/0053697 A1 * | 3/2003 | Aylward et al. | 382/203 |
| 2003/0099391 A1 * | 5/2003 | Bansal et al. | 382/131 |
| 2003/0122823 A1 | 7/2003 | Howson | |
| 2003/0123713 A1 | 7/2003 | Geng | |
| 2003/0193527 A1 | 10/2003 | Pharr | |
| 2004/0087853 A1 | 5/2004 | Fujisawa | |
| 2004/0171931 A1 * | 9/2004 | Barth et al. | 600/425 |
| 2004/0249270 A1 * | 12/2004 | Kondo et al. | 600/425 |
| 2005/0018902 A1 | 1/2005 | Liang | |
| 2005/0031194 A1 | 2/2005 | Lee et al. | |
| 2005/0063582 A1 | 3/2005 | Park et al. | |
| 2005/0110748 A1 | 5/2005 | Boeing et al. | |
| 2005/0113679 A1 * | 5/2005 | Suryanarayanan et al. | 600/425 |
| 2005/0122343 A1 * | 6/2005 | Bailey et al. | 345/619 |
| 2005/0147280 A1 | 7/2005 | Yan et al. | |
| 2005/0213820 A1 | 9/2005 | Liu et al. | |
| 2005/0276455 A1 * | 12/2005 | Fidrich et al. | 382/128 |
| 2005/0286750 A1 * | 12/2005 | Dehmeshki | 382/131 |
| 2006/0013482 A1 * | 1/2006 | Dawant et al. | 382/173 |
| 2006/0031372 A1 | 2/2006 | Krishnan et al. | |
| 2006/0067573 A1 | 3/2006 | Parr et al. | |
| 2006/0119600 A1 | 6/2006 | Lokovic et al. | |
| 2006/0203959 A1 | 9/2006 | Spartiotis et al. | |
| 2006/0239400 A1 | 10/2006 | Sukovic et al. | |
| 2006/0275740 A1 * | 12/2006 | Singh et al. | 433/215 |
| 2007/0279435 A1 * | 12/2007 | Ng et al. | 345/624 |
| 2008/0057478 A1 | 3/2008 | Choi | |
| 2009/0060299 A1 * | 3/2009 | Hibbard et al. | 382/128 |

FOREIGN PATENT DOCUMENTS

| | | |
|---|---|---|
| JP | 09-020085 | 1/1997 |
| JP | 11-009590 | 1/1999 |
| JP | 11-299782 | 11/1999 |
| JP | 2004-313576 | 11/2004 |
| JP | 2005-160503 | 6/2005 |
| JP | 2006-180944 | 7/2006 |
| WO | WO2006/008089 A1 | 1/2006 |
| WO | WO2007/134129 A2 | 11/2007 |

* cited by examiner

SYSTEM AND METHOD FOR LOCATING ANATOMIES OF INTEREST IN A 3D VOLUME

FIELD OF THE INVENTION

This invention relates generally to a system and method for displaying curved cross-sections of a 3D volume, and more specifically, to a system and method for dynamically modifying and displaying a curved cut plane of the 3D volume for locating items or sections of interest within the 3D volume.

BACKGROUND OF THE INVENTION

Technologies exist for obtaining 3D volume data representative of the internals of a physical object. For example, computer tomography (also known as a CAT scan) technology may be employed for generating a 3D image of the internals of a human body. The obtained 3D volume data may be processed and different cross-sectional images of the internals of the object viewed and manipulated by medical personnel to make diagnosis and plan medical procedures relating to the object. For example, the various images may be used in the dental field to view the bone structures of a person's skull and locate the mandibular nerve canal prior to placing a tooth implant.

Current mechanisms for locating items or sections of interest from 3D volume data are cumbersome and time-intensive. For example, with current mechanisms, a doctor or technician may make an educated guess as to a path in the 3D volume that contains the anatomy of interest, generate a cut plane of the 3D volume that intersects the selected path, and display a cross-sectional image of the 3D volume along the cut plane. If the initial guess does not exactly cut through the anatomy or sections of interest, the user modifies the path in and/or out of the volume in an attempt to more exactly locate the anatomy or sections of interest. The modification of the path results in the entire image data being reconstructed as a new cut plane is generated and a new cross-sectional image of the 3D volume along the new cut plane is displayed. This results in a noticeable time lag from the moment the user makes a change to a selected path to the moment the updated image is displayed. This trial and error process in locating anatomy or sections of interest is therefore very time consuming and tedious.

Current technologies also allow display of a 2D projection of volume image. A user selects a sub-area within a main projection, and displays different depths of the sub-area in relation to the projection plane by traversing different sub-projections that correspond to the selected sub-area. The sub-projections are stacked one behind another, and each provides information of an image plane that runs parallel to the main projection plane. The image displayed in the sub-projections, however, is not continuous with the surrounding data in the main projection, causing an incongruency in the overall image.

Accordingly, what is desired is a system and method for dynamically manipulating a curved cut plane intersecting a 3D volume for browsing different depths of the volume in relation to the plane while maintaining continuity of the image displayed to the user. It is also desirable to have a system and method for speeding the process of finding objects or sections of interest within the 3D volume by minimizing the time lag from the moment a user modifies the curved cut plane and the modified image is displayed to the user.

SUMMARY OF THE INVENTION

The present invention is directed to a computer-implemented method, system, and article of manufacture for locating an object or section of interest within a 3D volume. 3D volume data is stored in a data store, and a first curved cut plane is identified in the 3D volume based on a user input. A first cross-section of the 3D volume along the first curved cut plane is projected onto a viewing plane based on the 3D volume data. A point on a path of a curve of the first curved cut plane is selected via a user input device, and the user device is moved away from the selected point for browsing different portions of the 3D volume in order to locate the object or section of interest. A portion of the curve is recalculated based on the detected movement, and a second curved cut plane is generated in response. A second cross-section of the 3D volume along the second curved cut plane is re-projected onto the viewing plane based on the 3D volume data. According to one embodiment, the recalculating and re-projecting are substantially in real time with the movement of the user input device.

According to one embodiment of the invention, the 3D volume data is computer tomography data, and the item or section of interest is a nerve canal in a person's mandible.

According to one embodiment of the invention, the viewing plane is a 2D viewing plane displaying a panoramic image of the first and second cross-sections.

According to one embodiment of the invention, the path of the curve is projected onto the 2D viewing plane, and the user selection is selection of the point on the viewing plane.

According to one embodiment of the invention, the modifying the curve further includes modifying a portion of the curve in a first direction within the 3D volume in response to a first movement of the user input device on the viewing plane; and modifying a portion of the curve in a second direction within the 3D volume in response to a second movement of the user input device on the viewing plane.

According to one embodiment of the invention, the recalculating and re-projecting are continuous with the movement of the user input device.

According to one embodiment of the invention, the point on the path is point P0 which has first x, y, and z-coordinate values, and a signed distance of the detected movement is H. The recalculating the portion of the curve includes expanding or contracting an area surrounding P0 as a function of H, and defining points P1 and P2 on a boundary of the expanded or contracted area. Points P1 and P2 are defined by second x, y, and z-coordinate values, wherein the x-coordinate values of P1 and P2 are functions of H, and the y-coordinate values of P1 and P2 are the same as the y-coordinate value of P0. The method also includes defining a point P3 having third x, y, and z-coordinate values. The x and y-coordinate values of P3 are the same as the x and y-coordinate values of P0, and the z-coordinate value of P3 is a function of H. A curve that passes through P1, P2, and P3 is then identified, and the second curved cut plane is generated based on the identified curve.

These and other features, aspects and advantages of the present invention will be more fully understood when considered with respect to the following detailed description, appended claims, and accompanying drawings. Of course, the actual scope of the invention is defined by the appended claims.

DETAILED DESCRIPTION

In general terms, an embodiment of the present invention provides an efficient mechanism for modifying a curved cut plane of a 3D volume to locate objects or sections of interest within the 3D volume intersected by the cut plane. The 3D volume may be, for example, the internals of a person's skull, and the cut plane may follow, for example, the person's jaw line for locating the nerve canal on the person's mandible. In another example, the 3D volume may be of a person's back, and the curved cut plane may follow the spine along the person's back. Other examples that do not involve the human body are also contemplated.

According to one embodiment of the invention, a cross-section of the 3D volume along an initially estimated curved cut plane is projected onto a flat viewing plane, and a panorama image of the cross-section is displayed to the user. If the initially estimated curved cut plane does not exactly intersect the object or section of interest, the user manipulates a user input device to modify the curve of the plane inward or outward in the 3D volume away from the projected plane. As the user manipulates the user input device, an affected portion of the curve is recalculated and a modified curved cut plane is reconstructed based on the recalculated curve for re-projecting a modified cross-section of the 3D volume in real time with the movement of the user input device. The user is therefore provided with instant visual feedback as the user moves the user input device to browse in and out within the 3D volume from the current projected plane.

According to one embodiment of the invention, the continuity of the curve followed by the cut plane is maintained as the user browses in and out within the 3D volume. Thus, unlike in the prior art where a user browsing deeper within a sub-area of a current projected plane loses continuity with the surrounding image, such continuity is maintained according to one embodiment of the invention.

Figure 1:
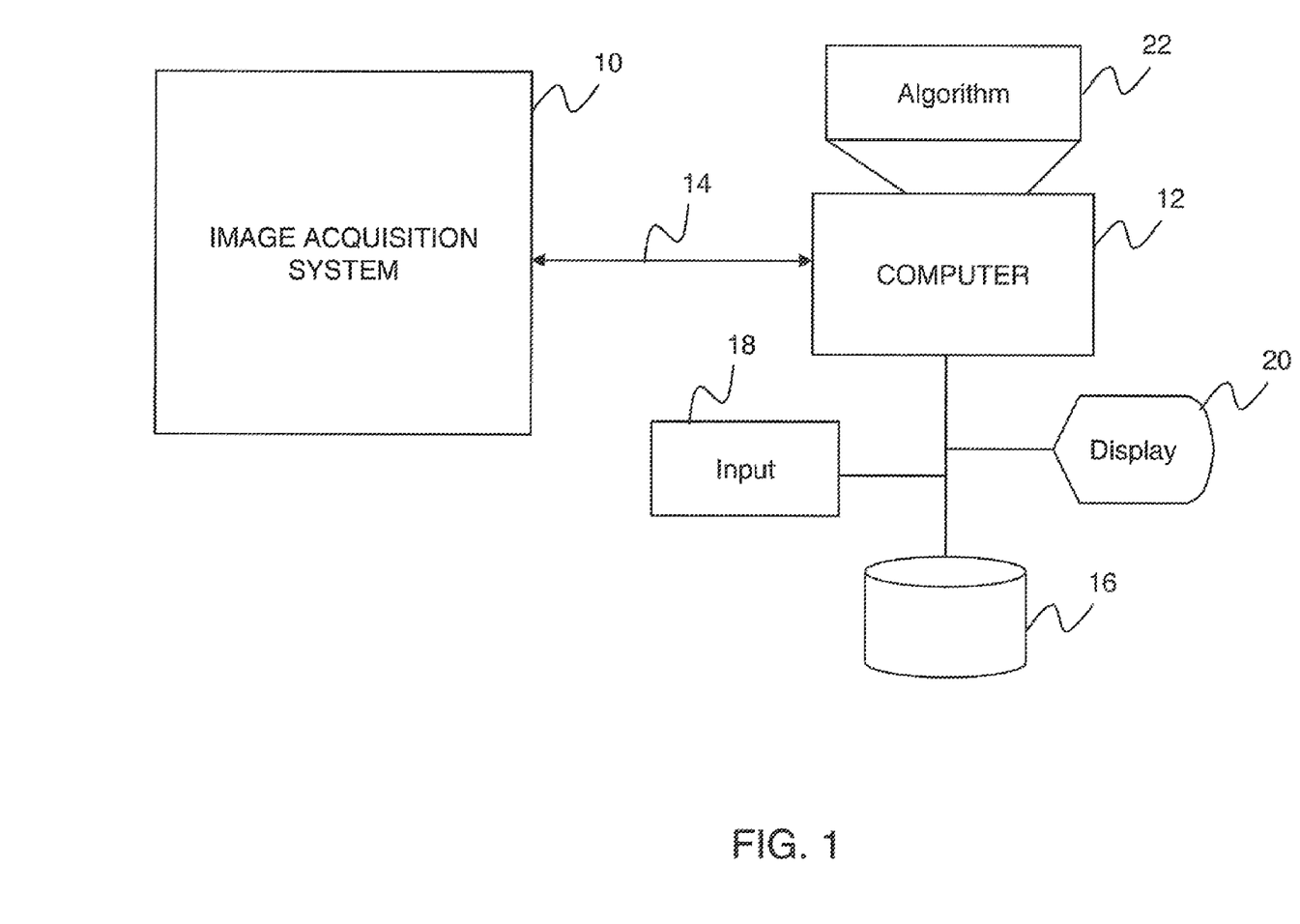
FIG. 1 is a schematic block diagram of a system for dynamically modifying and displaying a curved cut plane of a 3D volumetric object according to one embodiment of the invention.

FIG. 1 is a schematic block diagram of a system for efficiently modifying and displaying a curved cut plane of a 3D volumetric object according to one embodiment of the invention where the curved cut plane has some plane thickness that may be considered. The system includes an image acquisition system 10 coupled to a system computer 12 over a communications link 14. The communications link 14 may be a direct wire, an infrared data port, a wireless communications link, global communications link such as the Internet, or any other communications medium known in the art.

The image acquisition system 10 may be an X-ray system, ultrasound system, magnetic resonance system, computer tomography (CT) system, Conebeam tomography system, multimodality imagining system, or the like, that provides imaging data of the internals of a physical object. The physical object may be a human body or any other body form which internal structure is not readily seen.

According to one embodiment, the image acquisition system 10 scans the physical object and produces imaging data as, for example, planar arrays of data points where one planar array is generated at each of a regular succession of adjacent "slices" through the object scanned by the system. The imaging data is processed by the system computer 12 and a model of the 3D volume reconstructed according any reconstruction algorithm known in the art. The 3D volume data is then stored in a mass storage device 16 for later analysis. The mass storage device may be a hard disk or disk array conventional in the art. Alternatively, the image acquisition system 10 may include the software and hardware necessary to reconstruct the 3D volume based on the acquired imaging data, and thus, may be configured to transmit the reconstructed model of the 3D volume to the system computer 12 for storage and analysis.

The system computer 12 includes one or more input devices 18 and one or more displays 20. The input device 18 may take the form of a keyboard, stylus, mouse, joystick, or any other input device conventional in the art including, for example, a voice input device. A user manipulates the user input device 18 to modify the curved plane to find one or more objects or sections of interest of the 3D volumetric object.

The display 20 may take the form of a computer monitor, television monitor, or any other type of display monitor conventional in the art. According to one embodiment of the invention, the display incorporates pressure sensitive (touchscreen) technology so that a user input may be provided by the user by merely touching certain portions of the screen. The display 20 displays images generated based on the 3D volume data stored in the mass storage device 16. The image may be, for example, a panoramic image of the curved cut plane that intersects the 3D volume.

The system computer 12 also includes a memory (not shown) or other non-transitory computer readable media for storing one or more algorithms 22 to be executed by a processor (not shown) coupled to the memory or other non-transitory computer readable media. The algorithm includes a curve modification algorithm and optionally, an image reconstruction algorithm. The image reconstructions algorithm is configured to reconstruct the 3D volume based on the imaging data provided by the image acquisition system 10. The curve modification algorithm is configured to modify a curved cut plane and display a cross-section of the 3D volume along the cut plane on a flat viewing plane in real time as the modifications occur.

Figure 2:
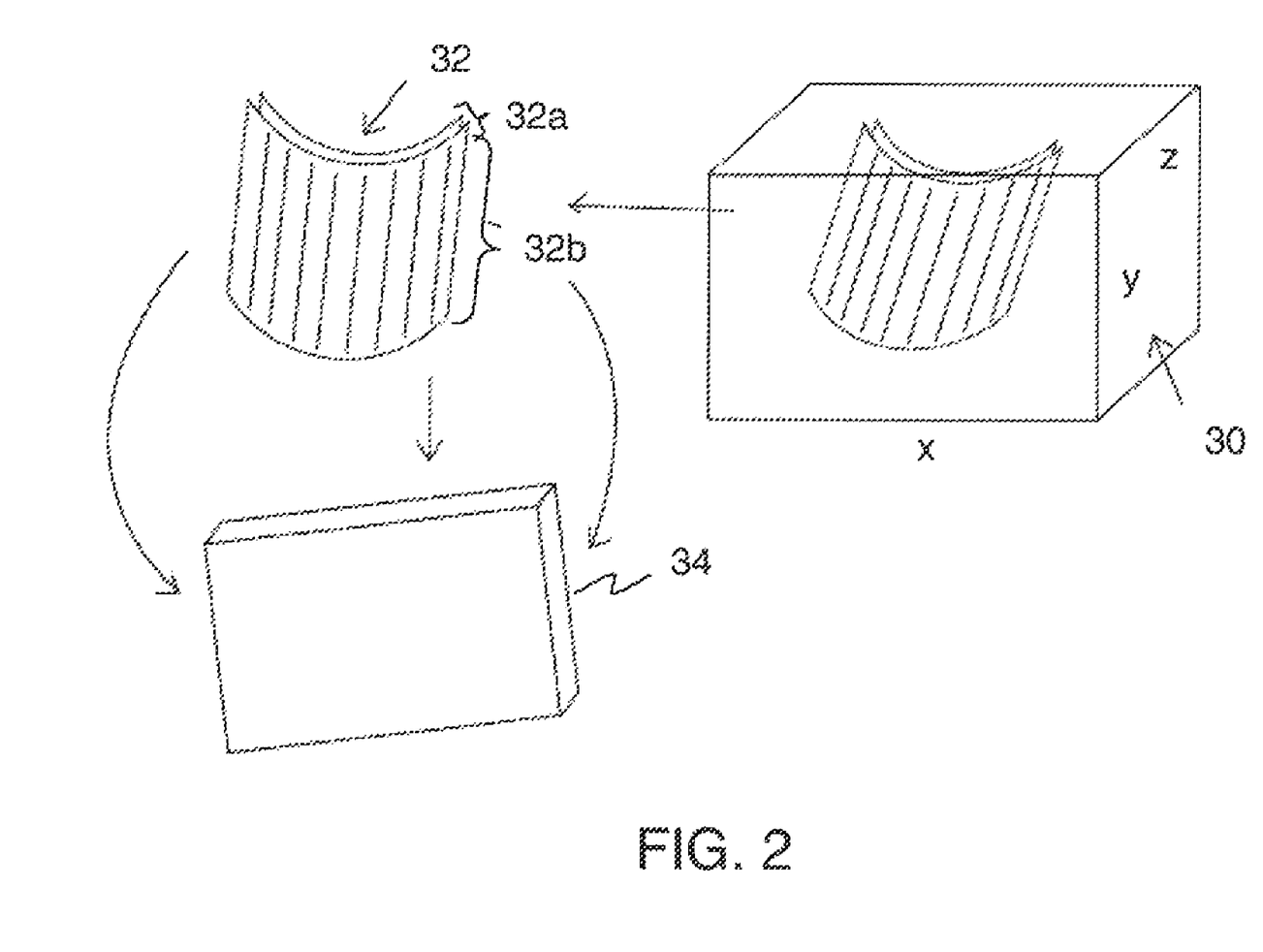
FIG. 2 symbolically illustrates an exemplary 3D volume as a cube having x, y, and z axes according to one embodiment of the invention.

FIG. 2 symbolically illustrates an exemplary 3D volume 30 as a cube having x, y, and z axes according to one embodiment of the invention. Given the 3D volume 30, an initial curved cut plane 32 is defined in the 3D volume based on an initial user input of the curve of the cut plane that is guessed to intersect an item or section of interest within the 3D volume. According to one embodiment of the invention, the curved cut plane 32 has a thickness 32a along the z-axis and a height 32b along the y-axis. According to one embodiment of the invention, the thickness depends on the diameter of the object or section of interest, and affects the prominence of the display of the object or section of interest. This is because the projected image is the average of a stack of image slices that are included in the thickness. Thus, for example, if object to be located is a nerve canal, the nerve canal is made more apparent on the projected image if the thickness is about the diameter of the nerve.

The width of the plane along the x-axis is assumed to span the entire width of the image, or may be bounded to a certain width. The portion of the 3D volume 30 cut by the curved cut plane 32 is projected onto a flat viewing plane 34 (also referred to as a projected plane) by any transformation algorithm conventional in the art.

Figure 3:
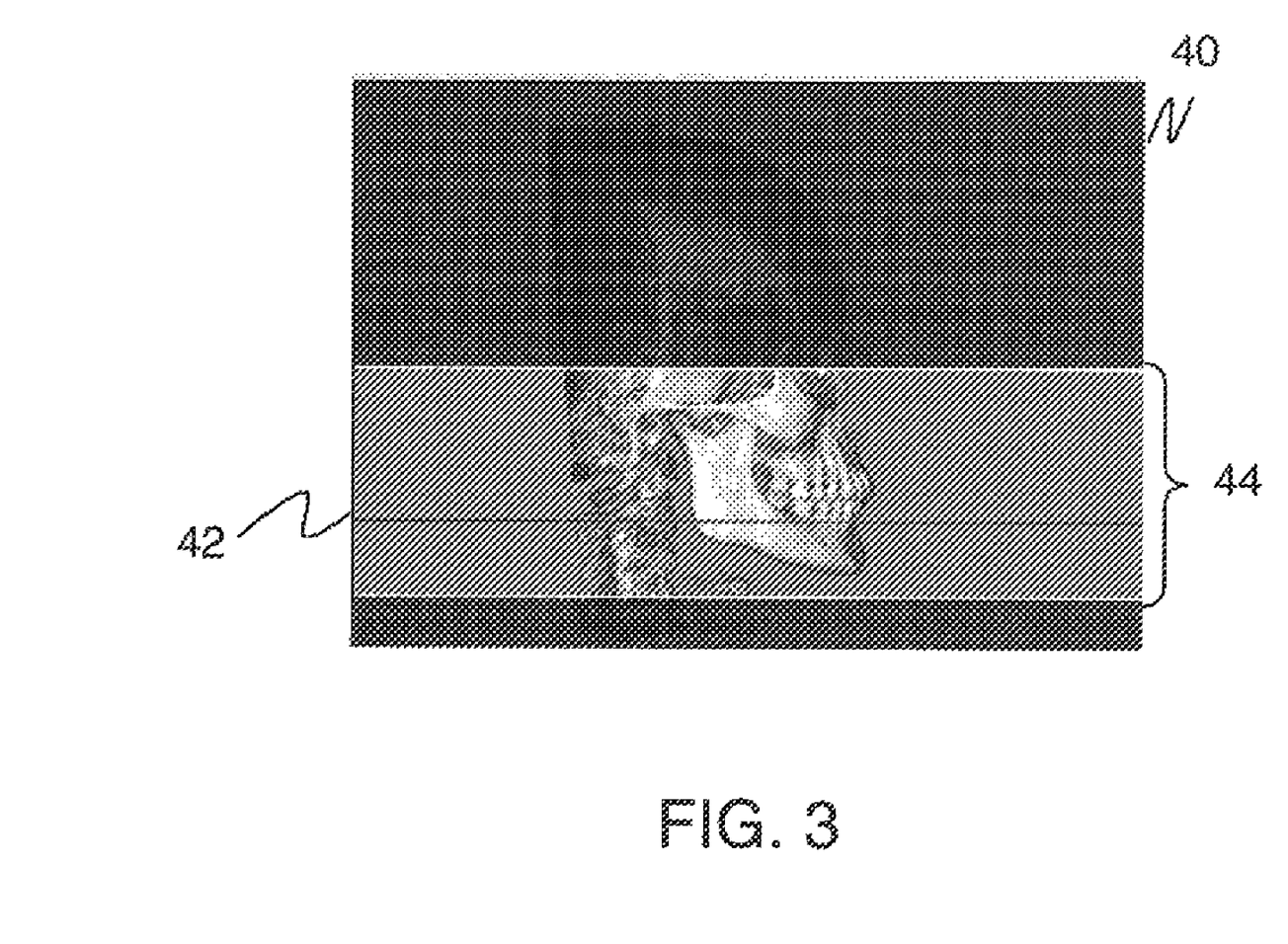
FIG. 3 is a photographic perspective view of an exemplary 3D image generated based on the 3D volume of FIG. 2 according to one embodiment of the invention.

FIG. 3 is a photographic perspective view of an exemplary 3D image 40 generated based on a 3D volume such as, for example, the 3D volume 30. A user manipulates the user input device 18 to bound the y-axis locations 44 of the curved cut plane by, for example, highlighting the 3D image along the y-axis location. As discussed above, the width of the plane along the x-axis is assumed to the entire width of the image.

According to one embodiment of the invention, the user manipulates the user input device 18 to position a line 42 within the bounds of the y-axis locations 44, and causes the system computer 12 to generate a cross-sectional image of a slice of the 3D volume along a plane perpendicular to the y-axis defined by the line 42.

Figure 4:
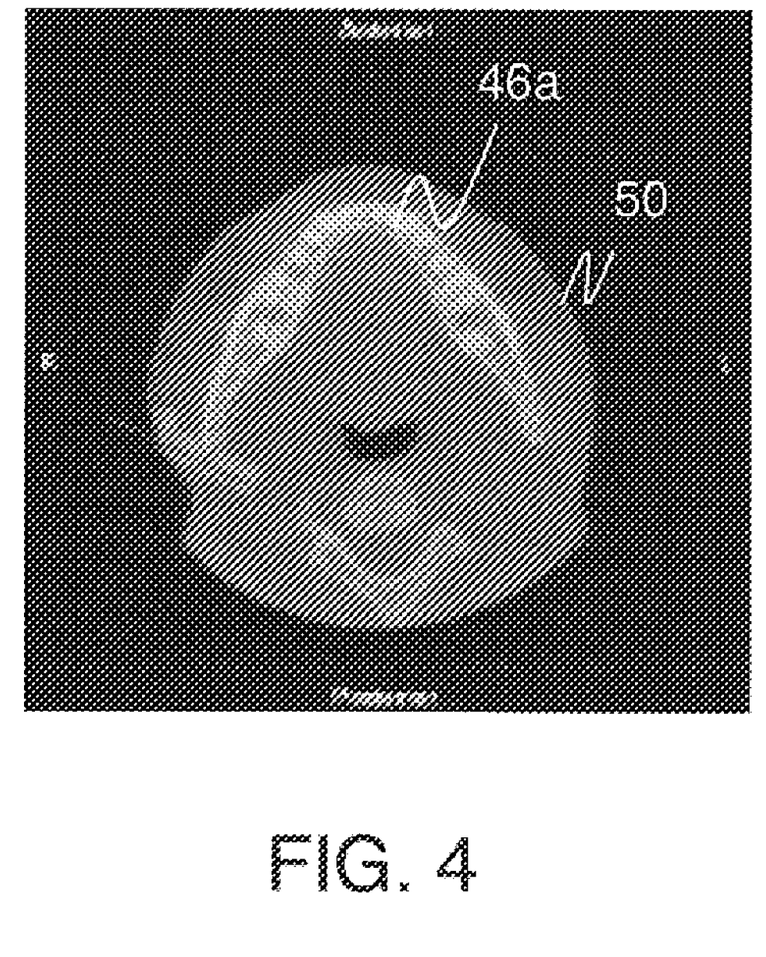
FIG. 4 is a photographic view of a slice of the 3D volume of FIG. 2 according to one embodiment of the invention.

FIG. 4 is a photographic view of a slice 50 of the 3D volume cut through the line 42 according to one embodiment of the invention. The view presented by the FIG. 4 is perpendicular to the direction of the cut. According to one embodiment of the invention, the user manipulates the user input device 18 to define on the slice 50 an initial path 46a of the curve of the plane 32. In this regard, the user takes a best guess as to where the plane would cut through a desired object or section and selects points on the slice to define the path of the curve. The initial cut plane 32 is constructed based on the initial path.

Figure 5:
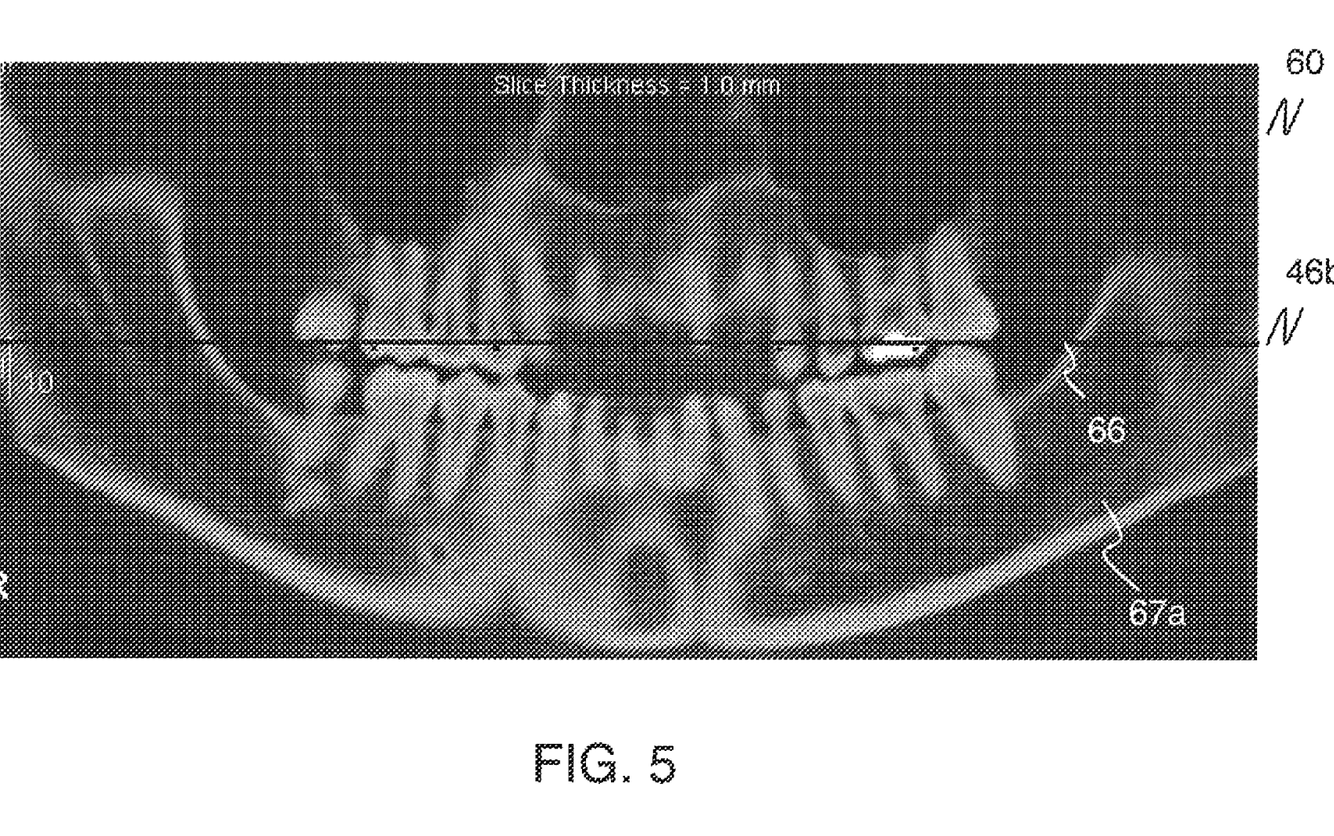
FIG. 5 is a photographic view of a projection of a curved cut plane onto a flat viewing plane according to one embodiment of the invention.

FIG. 5 is a photographic view of a projection of the curved cut plane 32 onto the flat viewing plane 34 according to one embodiment of the invention. The flat viewing plane 34 provides a panorama image 60 of the 3D volume along the curved cut plane 32. The height of the panorama image 60 is bounded by the height 32b of the cut plane 32 along the y-axis.

According to one embodiment of the invention, the markings made by the user to define the path 46a of the curved cut plane 32 is also projected onto the panorama image 60 as a straight path 46b.

The initial guess of the path 46a of the curve of the plane 32 may cut through none, some, or all of the desired object or section of the 3D volume. In this illustration, only a portion of the desired object, e.g. nerve canal 67a, is shown via the initial guess.

If the projection of the cut plane does not reveal all of the desired object or section, the user manipulates the user input device 18 to browse in and out of the 3D volume from the projected plane until all of the desired object or section is revealed. In this regard, the user clicks on a particular point 66 on the projected path 46b, and moves the user input device (e.g. a mouse) downward on the projected plane to signify browsing out of the 3D volume from the projected plane, or upward on the projected plane to signify browsing into the 3D volume from the projected plane. A person of skill in the art should recognize that any other mechanism may be employed to signify the browsing and out of the 3D volume such as, for example, selection of specific buttons, particular click patterns, and/or the like.

As the user drags the user input device 18 from the selected point 66, the curve modification algorithm stored in the system computer 12 recalculates the portion of the curve surrounding the selected point and reconstructs the curved cut plane based on the modified curve in real time with the movement of the user input device. The reconstructed curved cut plane is also re-projected and re-shown on the flat viewing plane in real time, continuous with the movement of the user input device. According to one embodiment of the invention, the curve modification algorithm recalculates and modifies only a small portion of the curve identified based on the location of the selected point 66 and the distance in which the user input device has moved so far, instead of recalculating the entire curve. This allows the reconstruction and re-projection of the curved cut plane to be performed quickly and repeatedly as the user input device moves. This in turn provides an instant visual feedback to the user for determining whether the reconstructed cut plane has cut through the object and/or section of interest to the user. Unlike in the prior art where browsing in and out within the 3D image merely allows a user to view different sub-projections of a particular sub-area but the overall image is not continuous, the curve modification algorithm according to one embodiment of the invention maintains the continuity of the curve of the cut plane for displaying different depths of the 3D volume along the continuous curve of the cut plane. Thus, overall image congruity is maintained.

Figure 6:
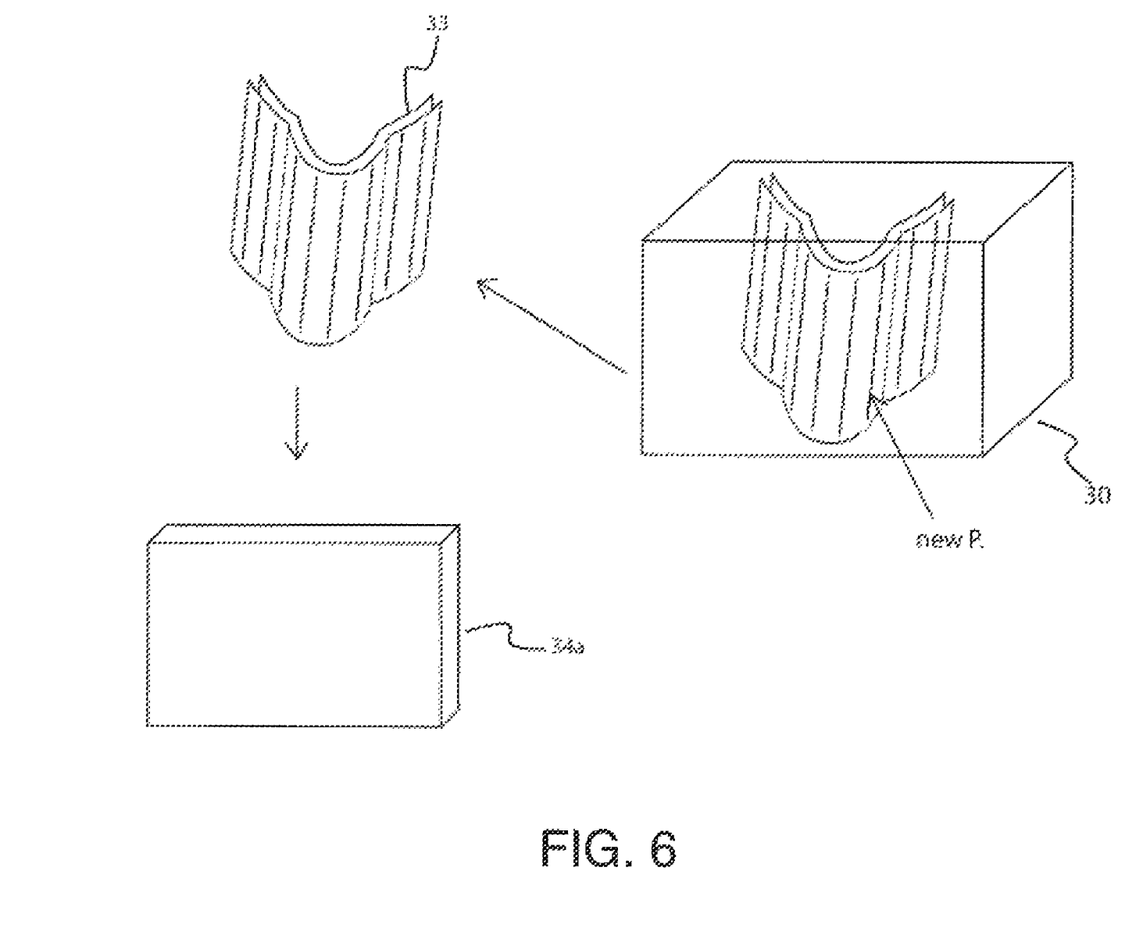
FIG. 6 illustrates a reconstructed curved cut plane after a portion of an initial curve has been modified according to one embodiment of the invention.
Figure 11:
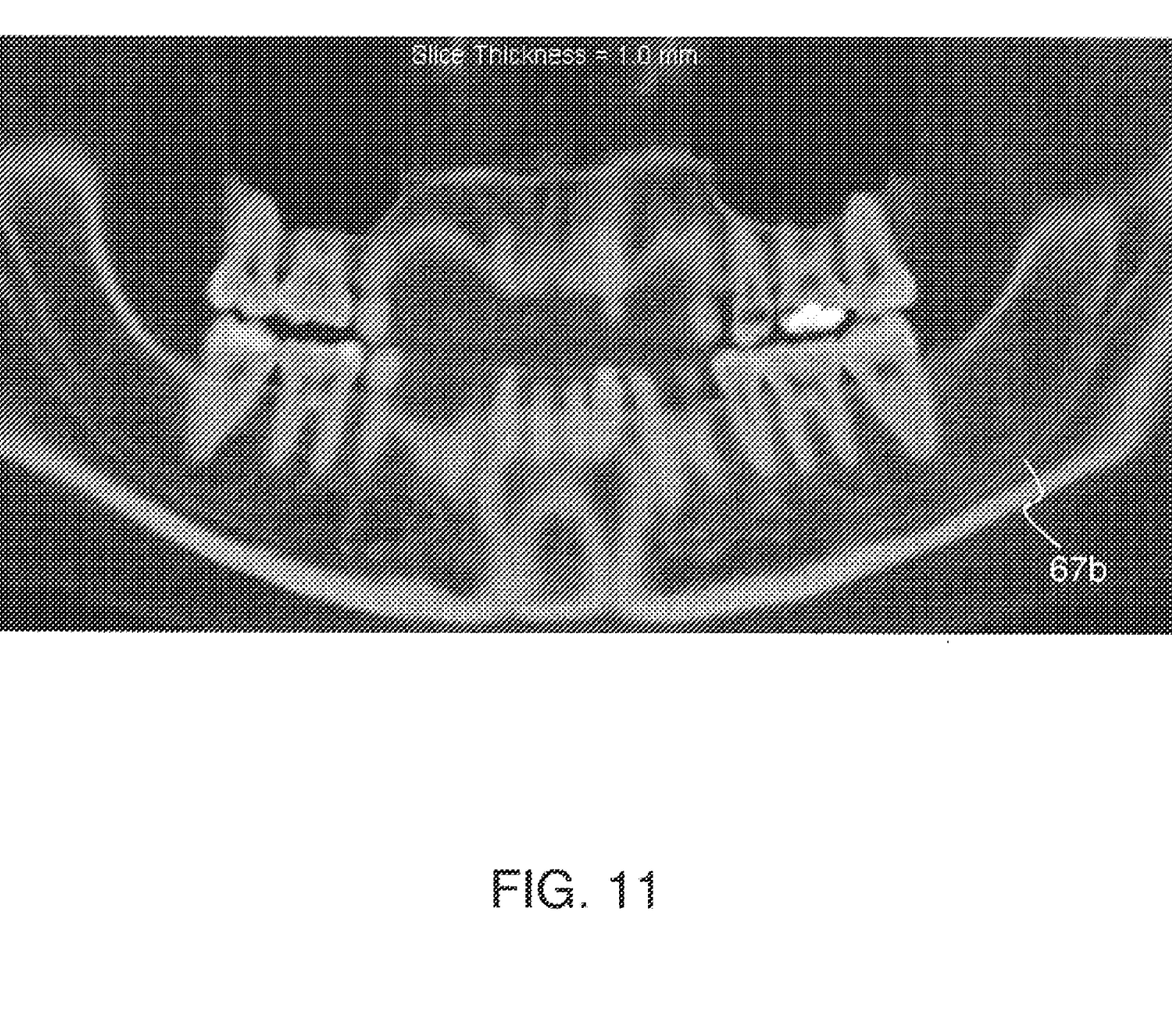
FIG. 11 is a photographic view of a re-projected cross-section of a 3D volume along a modified curved cut plane according to one embodiment of the invention.

FIG. 6 illustrates a reconstructed curved cut plane 33 based on the modified path of the curve according to one embodiment of the invention. A cross-section of the 3D volume 30 along the modified curved cut plane 33 is then re-projected onto the flat viewing plane 34a using any transformation algorithm conventional in the art. FIG. 11 is a photographic view of the re-projected cross-section of the 3D volume 30 along the modified curved cut plane according to one embodiment of the invention. In this example, all of the desired object, e.g. the entire nerve canal 67b, is displayed after one or more modifications of the curved cut plane.

Figure 7:
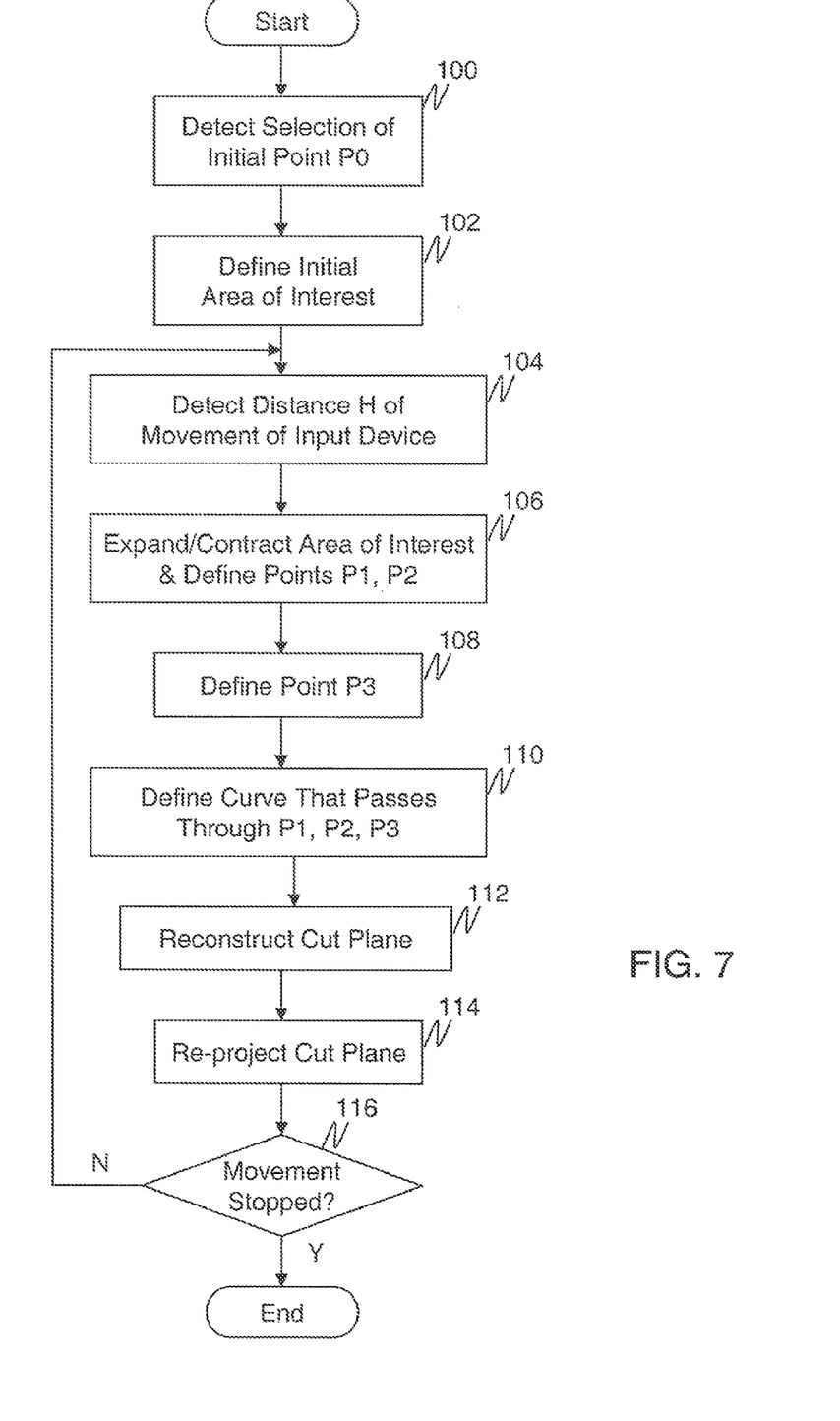
FIG. 7 is a flow diagram of a curve modification process provided by a curve modification algorithm for generating a modified curve cut plane according to one embodiment of the invention.

FIG. 7 is a flow diagram of a curve modification process provided by the curve modification algorithm for generating the modified curved cut plane 33 according to one embodiment of the invention. In step 100, the process detects selection of a point P0 on the projected path 46b of the projected plane P 34(b). In step 102, the process defines an initial area of interest based on the location of point P0. The initial area of interest may be a predetermined distance away from point P0 in opposite directions on the x-axis.

In step 104 the process detects movement of the user input device 18 according to any conventional mechanism known in the art, and determines a signed distance H of a current movement of the user input device on the projected plane P from the initial point P0, where the sign of H is negative if the movement is above P0, and the sign of H is positive if the movement is on or below P0, or vise versa.

In step 106, the initial area of interest is expanded, contracted, or stays fixed, as a function of H, and new points P1 and P2 defining the boundary of the new area of interest on the projected plane P are identified. According to one embodiment of the invention, the x-coordinate values of the points P1 and P2 are functions of H, and the y-coordinate values of the points are the same as the y-coordinate value of P0. Functions F1(H) and F2(H) for respectively determining the x-coordinate values of the points P1 and P2 may be as simple as F1(H)=x-coordinate of P0−k and F2(H)=x-coordinate of P0+k, where k is some positive constant. According to another embodiment, F1(H)=(x-coordinate of P0)−sqrt(|H|) and F2(|H|)=(x-coordinate of P0)+sqrt(|H|).

In step 108, point P3 is determined based on a movement away perpendicularly from the projected plane P on the z-axis. According to one embodiment of the invention, the x and y-coordinate values of point P3 are the same as the x and y-coordinate values of point P0. The z-coordinate value of P3 is a function of H. A function F3(H) for determining the z-coordinate value of P3 may be, for example, (z-coordinate of P0)+H.

Points P1, P2, and P3 now define a new plane on the 3D volume, and in step 110, the process maps a line segment connecting P1 and P2 to a curve that passes through P1, P2, and P3. This curve may be defined using a standard interpolating polynomial curve, or any other continuous interpolating curve known in the art. In this manner, only a portion of the initial curve is reprocessed and regenerated, allowing the reconstructing and re-projecting of a modified curved cut plane to be faster and more efficient.

In step 112, the curved cut plane is reconstructed based on the modified curve, and in step 114, a cross-section of the 3D volume along the reconstructed curved cut plane is re-projected onto a flat viewing plane 34a.

According to one embodiment of the invention, the process of FIG. 7 occurs in real time with the movement of the user input device. The speed in which the modified curved cut plane is reconstructed and re-projected depends on the processing speed of the computer. In step 116, a determination is made as to whether the movement of the user input device has stopped. If the answer is YES, the process ends. Otherwise, the process loops back to step 104 to reconstruct and re-project the cut plane for a new value of H.

Figure 8:
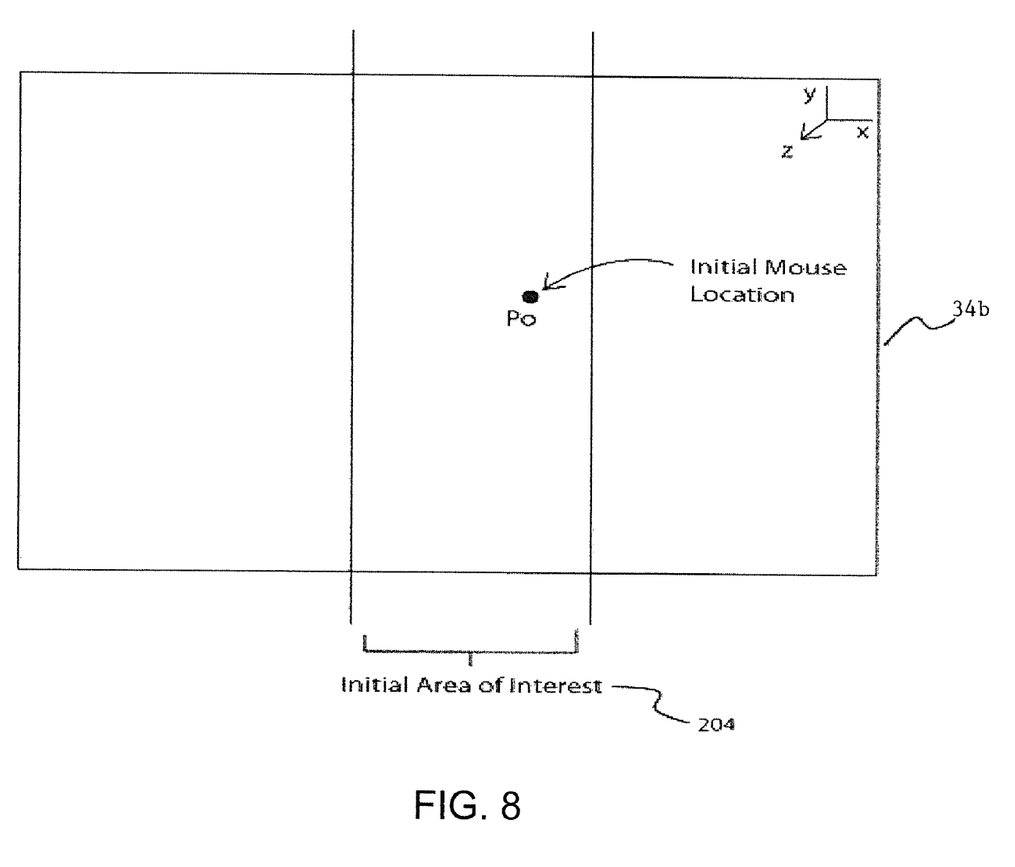
FIG. 8 illustrates a projected plane with an initial point P0 selected by a user via a user input device.

FIG. 8 illustrates the projected plane P 34 with an initial point P0 selected via the user input device. An initial area of interest 204 is then determined based on the initial point P0.

Figure 9:
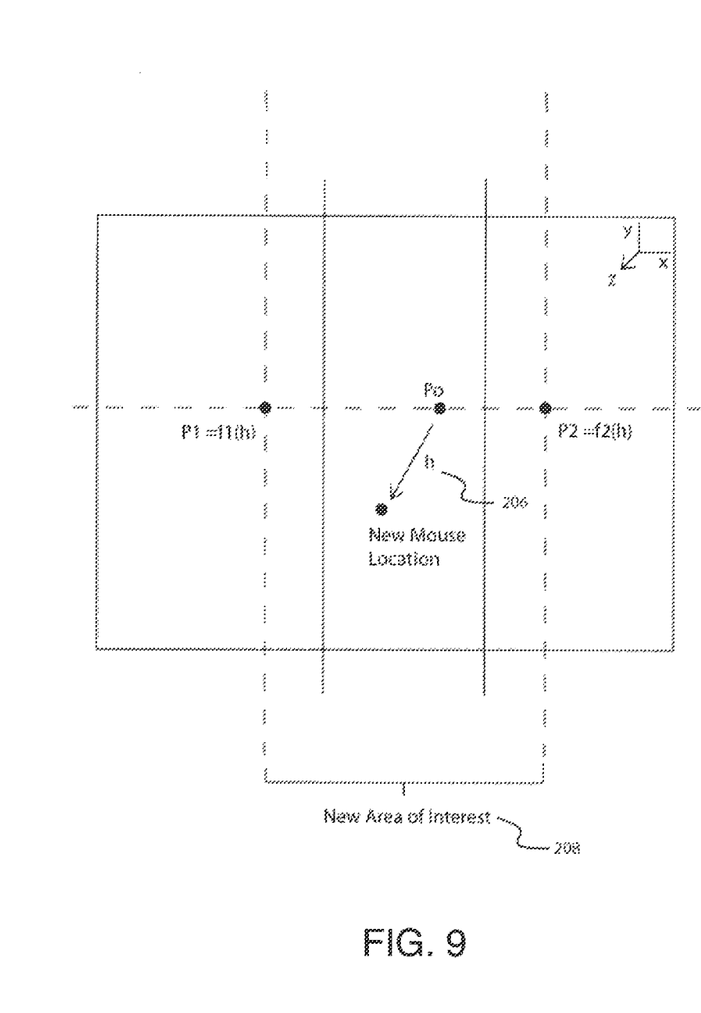
FIG. 9 illustrates movement of the user input device of FIG. 8 from the selected point P0.

FIG. 9 illustrates movement of the user input device from P0 by a distance of H 206. A new area of interest 208 is then defined with points P1 and P2 located at the boundary of the new area of interest. The x-coordinate values of points P1 and P2 are respectively determined by F1(H) and F2(H).

Figure 10A:
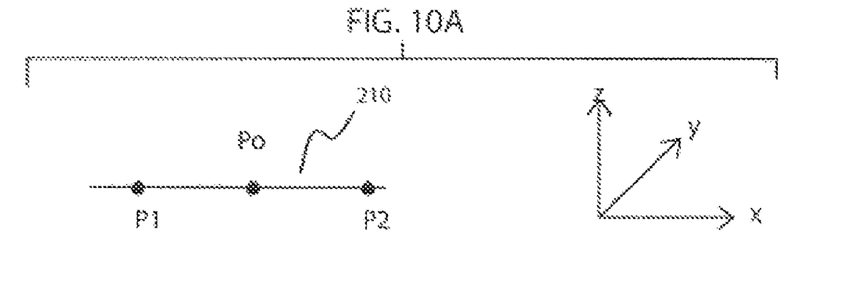
FIG. 10A illustrates newly generated points P1 and P2 on the projected plane of FIG. 8, and a line segment connecting points P1 and P2.
Figure 10B:
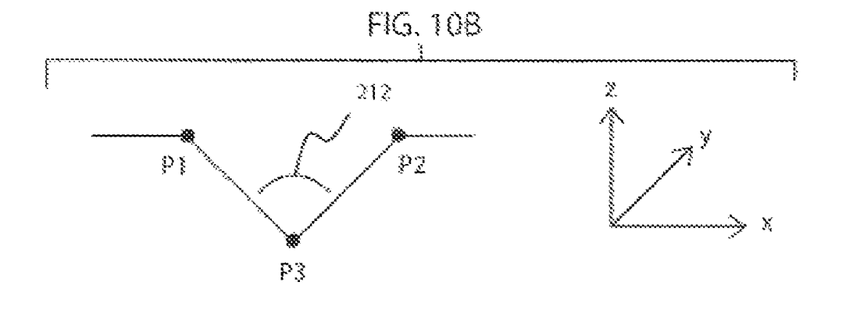
FIGS. 10B-10C illustrates a newly generated point P3, and alternative curves that may pass through points P1, P2, and P3.
Figure 10C:
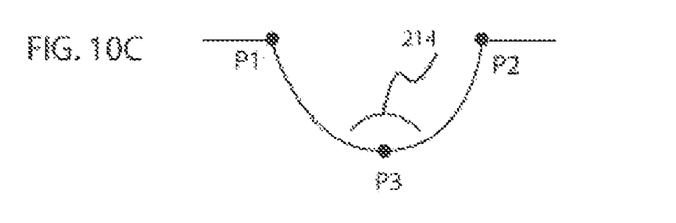

FIGS. 10A-10C illustrates the creation of a new curve that passes through points P1, P2, and P3. First, as illustrated in FIG. 10A, a line segment 210 connecting points P1 and P2 is generated. This line segment 210 is then mapped to a first type of curve as illustrated in FIG. 10B, or to a second type of curve as illustrated in FIG. 10C. According to FIG. 10B, the curve is made up of line segments 212 defined via a first degree polynomial. According to FIG. 10C, the curve is a parabola 214 defined via a second degree polynomial.

Figure 10D:
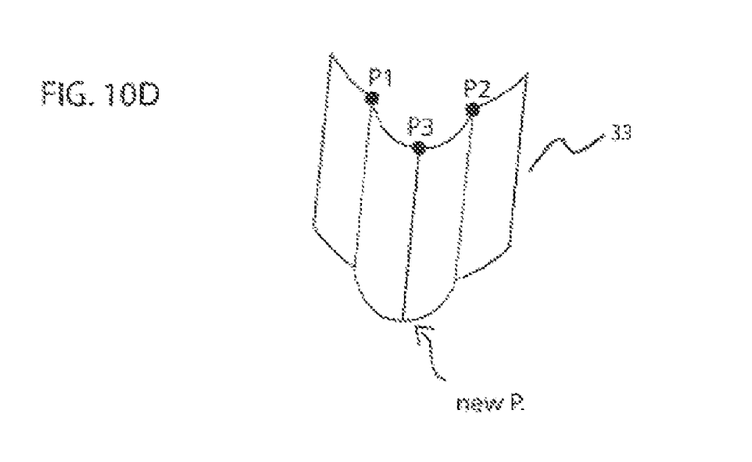
FIG. 10D illustrates a reconstructed curved cut plane based on the curve generated in FIG. 10C according to one embodiment of the invention.

FIG. 10D illustrates the reconstructed curved cut plane 33 based on the curve generated in FIG. 10C according to one embodiment of the invention.

Although this invention has been described in certain specific embodiments, those skilled in the art will have no difficulty devising variations to the described embodiment which in no way depart from the scope and spirit of the present invention. For example, while the system described herein is used for identifying anatomical features of interest, a person of skill in the art should recognize that the present invention may also be used for industrial processes as will be understood by those skilled in the art. Furthermore, although the algorithm 22 is described as being hosted by the computer 12, a person of skill in the should recognize that the image algorithm 22 may be hosted by the image acquisition system 10 instead of the computer 12.

Furthermore, to those skilled in the various arts, the invention itself herein will suggest solutions to other tasks and adaptations for other applications. It is the Applicant's intention to cover by claims all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive, the scope of the invention to be indicated by the appended claims and their equivalents rather than the foregoing description.

What is claimed is:

1. A computer-implemented method for locating an object or section of interest within a 3D volume, the method comprising:
   storing 3D volume data in a data store;
   identifying, by a computer device, a first curved cut plane in the 3D volume based on a user input, the first curved cut plane following a first curved path;
   projecting, by the computer device, onto a viewing plane a first cross-section of the 3D volume along the first curved cut plane following the first curved path based on the 3D volume data, wherein the projecting onto the viewing plane displays a flattened display of the first curved cut plane following the first curved path;
   receiving, by the computer device, a user selection on the flattened display of the first curved cut plane following the first curved path, via a user input device, wherein the user selection identifies a selected point on the flattened display;
   detecting, by the computer device, movement of the user input device away from the selected point;
   recalculating, by the computer device, a portion of the curve based on the detected movement and generating a second curved cut plane following a second curved path in response; and
   re-projecting, by the computer device, onto the viewing plane a second cross-section of the 3D volume along the second curved cut plane following the second curved path based on the 3D volume data, wherein the recalculating and re-projecting are substantially in real time with the movement of the user input device.

2. The method of claim 1, wherein the 3D volume data is computer tomography data, and the item or section of interest is a nerve canal in a person's mandible.

3. The method of claim 1, wherein the viewing plane is a 2D viewing plane displaying a panoramic image of the first and second cross-sections.

4. The method of claim 3, wherein the path of the curve is projected onto the 2D viewing plane.

5. The method of claim 1, wherein the modifying the curve further comprises:
   modifying a portion of the curve in a first direction within the 3D volume in response to a first movement of the user input device on the flattened display; and
   modifying a portion of the curve in a second direction within the 3D volume in response to a second movement of the user input device on the flattened display.

6. The method of claim 1, wherein the recalculating and re-projecting are continuous with the movement of the user input device.

7. A computer-implemented method for locating an object or section of interest within a 3D volume, the method comprising:
    storing 3D volume data in a data store;
    identifying, by a computer device, a first curved cut plane in the 3D volume based on a user input;
    projecting, by the computer device, onto a viewing plane a first cross-section of the 3D volume along the first curved cut plane based on the 3D volume data;
    receiving, by the computer device, a user selection of a point on a path of a curve of the first curved cut plane via a user input device;
    detecting, by the computer device, movement of the user input device away from the selected point;
    recalculating, by the computer device, a portion of the curve based on the detected movement and generating a second curved cut plane in response; and
    re-projecting, by the computer device, onto the viewing plane a second cross-section of the 3D volume along the second curved cut plane based on the 3D volume data,
    wherein the recalculating and re-projecting are substantially in real time with the movement of the user input device,
    wherein the point on the path is point P0 having first x, y, and z-coordinate values, a signed distance of the detected movement is H, and the recalculating the portion of the curve comprises:
        expanding or contracting an area surrounding P0 as a function of H, and defining points P1 and P2 on a boundary of the expanded or contracted area, P1 and P2 respectively having second and third x, y, and z-coordinate values, wherein the x-coordinate values of P1 and P2 are functions of H, and the y-coordinate values of P1 and P2 are the same as the y-coordinate value of P0;
        defining a point P3 having fourth x, y, and z-coordinate values, wherein the x and y-coordinate values of P3 are the same as the x and y-coordinate values of P0, and the z-coordinate value of P3 is a function of H; and
        identifying a curve that passes through P1, P2, and P3, wherein the second curved cut plane is generated based on the identified curve.

8. A computer system for locating an object or section of interest within a 3D volume, the system comprising:
    a data store storing 3D volume data;
    a processor; and
    a memory operably coupled to the processor and storing program instructions therein, the processor being operable to execute the program instructions, the program instructions including:
        identifying a first curved cut plane in the 3D volume based on a user input, the first curved cut plane following a first curved path;
        projecting onto a viewing plane a first cross-section of the 3D volume along the first curved cut plane following the first curved path based on the 3D volume data, wherein the projecting onto the viewing plane displays a flattened display of the first curved cut plane following the first curved path;
        receiving a user selection on the flattened display of the first curved cut plane following the first curved path, via a user input device, wherein the user selection identifies a selected point on the flattened display;
        detecting movement of the user input device away from the selected point;
        recalculating a portion of the curve based on the detected movement and generating a second curved cut plane following a second curved path in response; and
        re-projecting onto the viewing plane a second cross-section of the 3D volume along the second curved cut plane following the second curved path based on the 3D volume data, wherein the recalculating and re-projecting is substantially in real time with the movement of the user input device.

9. The system of claim 8, wherein the 3D volume data is computer tomography data, and the item or section of interest is a nerve canal in a person's mandible.

10. The system of claim 8, wherein the viewing plane is a 2D viewing plane displaying a panoramic image of the first and second cross-sections.

11. The system of claim 10, wherein the path of the curve is projected onto the 2D viewing plane.

12. The system of claim 8, wherein the computer program instructions for modifying the curve further include:
    modifying a portion of the curve in a first direction within the 3D volume in response to a first movement of the user input device on the flattened display; and
    modifying the portion of the curve in a second direction within the 3D volume in response to a second movement of the user input device on the flattened display.

13. The system of claim 8, wherein the recalculating and re-projecting are continuous with the movement of the user input device.

14. A computer system for locating an object or section of interest within a 3D volume, the system comprising:
    a data store storing 3D volume data;
    a processor; and
    a memory operably coupled to the processor and storing program instructions therein, the processor being operable to execute the program instructions, the program instructions including:
        identifying a first curved cut plane in the 3D volume based on a user input;
        projecting onto a viewing plane a first cross-section of the 3D volume along the first curved cut plane based on the 3D volume data;
        receiving a user selection of a point on a path of a curve of the first curved cut plane via a user input device;
        detecting movement of the user input device away from the selected point;
        recalculating a portion of the curve based on the detected movement and generating a second curved cut plane in response; and
        re-projecting onto the viewing plane a second cross-section of the 3D volume along the second curved cut plane based on the 3D volume data, wherein the recalculating and re-projecting is substantially in real time with the movement of the user input device,
    wherein the point on the path is point P0 having first x, y, and z-coordinate values, a signed distance of the detected movement is H, and the computer program instructions for recalculating the portion of the curve comprises:
        expanding or contracting an area surrounding P0 as a function of H, and defining points P1 and P2 on a boundary of the expanded or contracted area, P1 and P2 respectively having second and third x, y, and z-coordinate values, wherein the x-coordinate values of P1 and P2 are functions of H, and the y-coordinate values of P1 and P2 are the same as the y-coordinate value of P0;

defining a point P3 having third-fourth x, y, and z-coordinate values, wherein the x and y-coordinate values of P3 are the same as the x and y-coordinate values of P0, and the z-coordinate value of P3 is a function of H; and identifying a curve that passes through P1, P2, and P3, wherein the second curved cut plane is generated based on the identified curve.

15. A non-transitory computer readable media embodying program instructions for execution by a data processing apparatus, the program instructions adapting a data processing apparatus for locating an object or section of interest within a 3D volume having 3D volume data stored in a data store, the program instructions comprising:

identifying a first curved cut plane in the 3D volume based on a user input, the first curved cut plane following a first curved path;

projecting onto a viewing plane a first cross-section of the 3D volume along the first curved cut plane following the first curved path based on the 3D volume data, wherein the projecting onto the viewing plane displays a flattened display of the first curved cut plane following the first curved path;

receiving a user selection on the flattened display of the first curved cut plane following the first curved path, via a user input device, wherein the user selection identifies a selected point on the flattened display;

detecting movement of the user input device away from the selected point;

recalculating a portion of the curve based on the detected movement and generating a second curved cut plane following a second curved path in response; and re-projecting onto the viewing plane a second cross-section of the 3D volume along the second curved cut plane following the second curved path based on the 3D volume data, wherein the recalculating and re-projecting are substantially in real time with the movement of the user input device.

16. The computer readable media of claim 15, wherein the 3D volume data is computer tomography data, and the item or section of interest is a nerve canal in a person's mandible.

17. The computer readable media of claim 15, wherein the viewing plane is a 2D viewing plane displaying a panoramic image of the first and second cross-sections.

18. The computer readable media of claim 17, wherein the path of the curve is projected onto the 2D viewing plane.

19. The computer readable media of claim 15, wherein the program instructions for modifying the curve further include:

modifying a portion of the curve in a first direction within the 3D volume in response to a first movement of the user input device on the flattened display; and modifying the portion of the curve in a second direction within the 3D volume in response to a second movement of the user input device on the flattened display.

20. The computer readable media of claim 15, wherein the recalculating and re-projecting are continuous with the movement of the user input device.

21. A non-transitory computer readable media embodying program instructions for execution by a data processing apparatus, the program instructions adapting a data processing apparatus for locating an object or section of interest within a 3D volume having 3D volume data stored in a data store, the program instructions comprising:

identifying a first curved cut plane in the 3D volume based on a user input;

projecting onto a viewing plane a first cross-section of the 3D volume along the first curved cut plane based on the 3D volume data;

receiving a user selection of a point on a path of a curve of the first curved cut plane via a user input device;

detecting movement of the user input device away from the selected point;

recalculating a portion of the curve based on the detected movement and generating a second curved cut plane in response; and re-projecting onto the viewing plane a second cross-section of the 3D volume along the second curved cut plane based on the 3D volume data, wherein the recalculating and re-projecting is substantially in real time with the movement of the user input device, wherein the point on the path is point P0 having first x, y, and z-coordinate values, a distance of the detected movement is H, and the program instructions for recalculating the portion of the curve comprises:

expanding or contracting an area surrounding P0 as a function of H, and defining points P1 and P2 on a boundary of the expanded or contracted area, P1 and P2 respectively having second and third x, y, and z-coordinate values, wherein the x-coordinate values of P1 and P2 are functions of H, and the y-coordinate values of P1 and P2 are the same as the y-coordinate value of P0;

defining a point P3 having fourth x, y, and z-coordinate values, wherein the x and y-coordinate values of P3 are the same as the x and y-coordinate values of P0, and the z-coordinate value of P3 is a function of H; and identifying a curve that passes through P1, P2, and P3, wherein the second curved cut plane is generated based on the identified curve.

* * * * *

UNITED STATES PATENT AND TRADEMARK OFFICE
CERTIFICATE OF CORRECTION

| | |
|---|---|
| PATENT NO. | : 7,978,191 B2 |
| APPLICATION NO. | : 11/860303 |
| DATED | : July 12, 2011 |
| INVENTOR(S) | : Swanwa Liao |

It is certified that error appears in the above-identified patent and that said Letters Patent is hereby corrected as shown below:

In the Claims

Column 11, Claim 14, line 1          Delete "third-"

Signed and Sealed this
Fourteenth Day of February, 2012

David J. Kappos
*Director of the United States Patent and Trademark Office*